United States Patent [19]

Indig et al.

[11] Patent Number: 5,192,414

[45] Date of Patent: Mar. 9, 1993

[54] ELECTRODE PROBE FOR USE IN AQUEOUS ENVIRONMENTS OF HIGH TEMPERATURE AND HIGH RADIATION

[75] Inventors: Maurice E. Indig, Fremont; Jerry F. Hanlon, Livermore, both of Calif.

[73] Assignee: General Electric Company, San Jose, Calif.

[21] Appl. No.: 633,748

[22] Filed: Dec. 20, 1990

[51] Int. Cl.$^5$ .............................................. G01N 27/30
[52] U.S. Cl. .................................... 204/400; 204/280; 204/286; 204/416; 204/435; 376/245; 376/256
[58] Field of Search ................... 204/280, 286, 297 R, 204/400, 415–419, 435; 376/245, 256

[56] References Cited

U.S. PATENT DOCUMENTS

| | | | |
|---|---|---|---|
| 3,413,209 | 11/1968 | Hersch | 204/415 |
| 3,486,996 | 12/1969 | Annand | 204/404 |
| 4,882,029 | 11/1989 | Eickmann | 204/297 R |
| 4,948,492 | 8/1990 | Niedrach et al. | 204/435 |

Primary Examiner—T. Tung
Attorney, Agent, or Firm—Robert R. Schroeder

[57] ABSTRACT

The present invention is addressed to an electrode for evaluating electrochemical potentials which has a robust structure particularly suiting it for employment within the rigorous environment of the reactor core of a nuclear power facility. The electrode of the present invention is comprised of five major segments: a metal cap electrode, an elongate annular metal jacket, an alumina retainer (i.e. an insulator), an annular metal transition sleeve, and a positioning and signal transfer assembly. The metal cap electrode has a tip and annulus extending therefrom formed from sidewalls having an interior surface. The elongate annular metal jacket has an annular retainer securing mouth at one end and an outlet at its opposite end. The alumina retainer has a recessed cap securing portion nestably secured to a portion of said cap electrode interior sidewall surface, and an oppositely-disposed recessed jacket securing portion nestably secured to the interior of said annular jacket retainer securing mouth. The retainer further has an access channel penetrating therethrough from said cap to said jacket securing portion. The annular metal transition sleeve has one end placed at the jacket outlet, the opposite end at the positioning and signal transfer assembly. A first insulated electrical conductor in electrical connection with the cap electrode extends through the retainer access channel and through the annular metal jacket to the jacket outlet. Finally, the positioning and signal transfer assembly is associated with the transition sleeve outlet for providing fit-up for said sleeve and for conveying electrical signals from said conductor. The elongated annular metal transition sleeve is interposed between said jacket and said positioning and signal transfer assembly.

18 Claims, 2 Drawing Sheets

FIG. 1
FIG. 2
FIG. 3
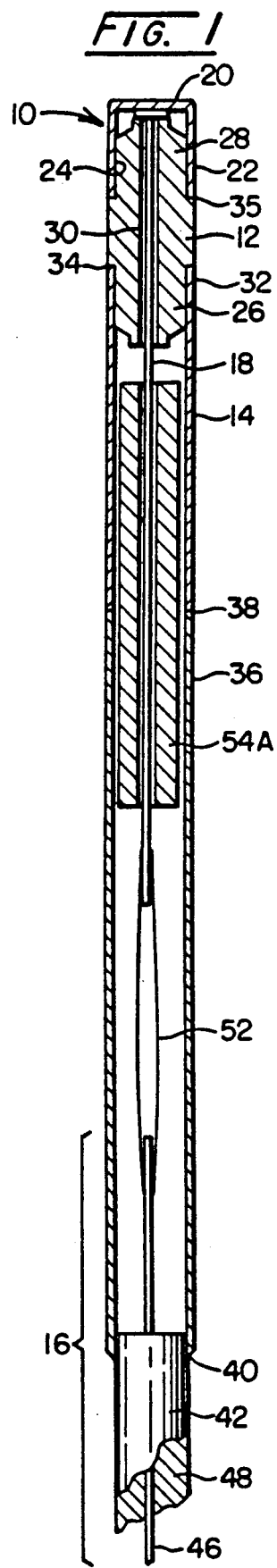
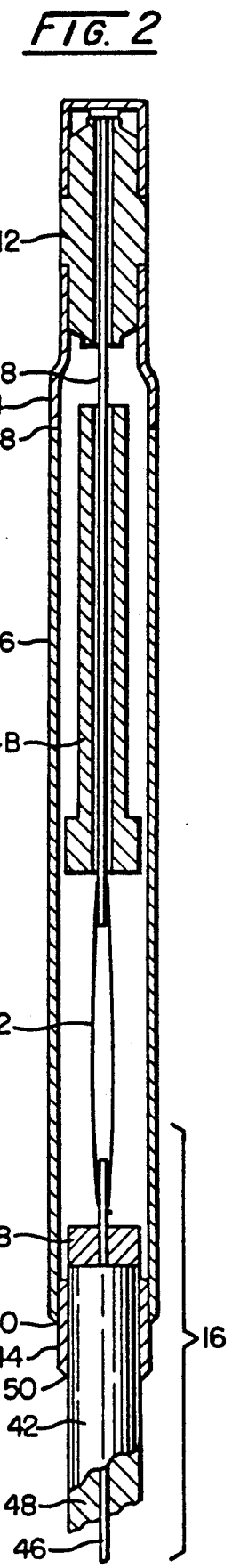
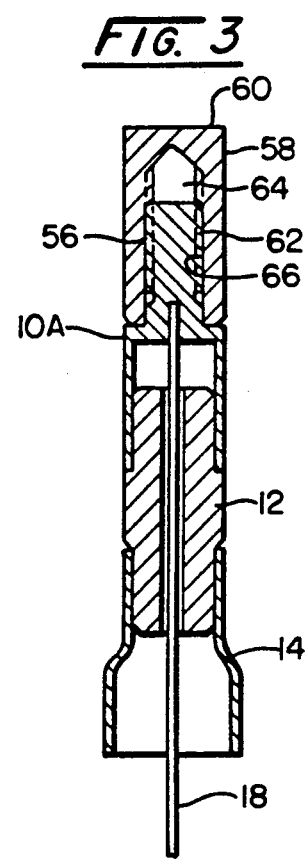

ELECTRODE PROBE FOR USE IN AQUEOUS ENVIRONMENTS OF HIGH TEMPERATURE AND HIGH RADIATION

BACKGROUND OF THE INVENTION

The nuclear power industry long has been engaged in a multitude of studies and investigations seeking improvement in the stamina and reliability of the materials and components forming a reactor based power system. One such investigation has been concerned with intergrannular stress corrosion cracking (IGSCC) which heretofore principally has been manifested in the water recirculation piping systems external to the radiation intense reactor core regions of nuclear facilities. Typically, the piping architecture of these external systems is formed of a stainless steel material. Generally, these studies have determined that three factors must occur in coincidence to create IGSCC promotional conditions. These factors are: (a) a sensitization of the metal (stainless steel), for example, such as caused by a chromium depletion at grain boundaries which may be caused by heat treatment in the course of normal processing of the material or by welding and like procedures; (b) the presence of tensile stress in the material; and (c) the oxygenated normal water chemistry (NWC) environment typically present in a boiling water reactor (BWR). By removing any one of these three factors, the IGSCC phenomenon is essentially obviated. Such removal particularly has been accomplished with respect to the latter, oxygenated environment factor through employment of an electrochemical potential monitoring approach combined with an associated hydrogen water chemistry (HWC) technique providing for a controlled addition or injection of hydrogen into the aqueous coolant environment.

Electrochemical potential monitoring is carried out employing paired electrochemical half-cell probes or electrodes which are mounted within the recirculation piping or in an external vessel which has its water source from the reactor water in the recirculation piping. The electrodes are accessed to the external environment through gland type mountings or the like. Where, as in the instant application, the electrode system of interest involves the potential from a metal corrosion electrode, then the reference electrode can conveniently be a metal-insoluble salt electrode, if the metal salt couple is chemically stable and if appropriate thermodynamic data is available. Accordingly, one of the thus-mounted probes which is configured as a reference electrode may be based, for example, on a silver/silver chloride half-cell reaction. Once the reference electrode half-cell is defined, the cell is completed with the sensing cell portion based upon a metal such as platinum or stainless steel. Calibration of the reference electrode and/or the electrode pair is carried out by thermodynamic evaluation and appropriate Nernst based electrochemical calculations in combination with laboratory testing within a known environment.

Half cell electrodes developed for use in reactor circulation piping traditionally have been configured with metal housings, high temperature ceramics, and polymeric seals such as Teflon brand polytetrafluoroethylene. These structures have performed adequately in the more benign and essentially radiation-free environments of recirculation piping.

Over the recent past, investigators have sought to expand the electrochemical potential (ECP) monitoring procedures to the severe environment of the fluid in the vicinity of the reactor core itself for the purpose of studying or quantifying the effect of hydrogen-water chemistry adjustment in mitigating irradiation assisted stress corrosion cracking (IASSC) as well as IGSCC. Within the reactor core, the monitoring electrode can be mounted, for example, with otherwise unemployed or in tandem with the traveling instrumentation probe (TIP) of available local power range monitors (LPRM) and the like. The monitors are located in severe, high temperature and radiation (typically $10^9$ R (rads) per hour gamma, $10^{13}$ R per hour neutron) environments. Probe structures of earlier designs are completely inadequate for this reactor core environment, both from a material standpoint and with respect to the critical need to prevent leakage of radioactive materials to the environment outside of the reactor vessel. One probe, however, that has a robust structure adequate for use in the rigorous environment of the reactor core of a nuclear power facility is disclosed in commonly-assigned U.S. Ser. No. 07/345,740, filed May 1, 1989, now U.S. Pat. No. 4,948,492. A critical feature of such probe design is the alumina (sapphire) post and post cap which are located inside of the crucible. Because of space limitations, the manufacturing processes which are performed inside the crucible, such as metalizing and brazing, cannot be controlled as well as the manufacturer would like. Inadequate metalizing and brazing at this interface often are not detected until the electrode fails prematurely either during final testing or in the field.

One of the most critical aspects of monitoring and controlling the electrochemical potential is during the introduction of hydrogen to the reactor. Therefore, the development of reference electrodes that can withstand the extreme radiation and the harsh high temperatures, high pressure aqueous environment and provide electrochemical potentials are directly determined by the introduction of the hydrogen, can provide process and operational control leading to elimination of IASCC in the core region and, if installed in the piping, control of the IGSCC in the reactor recirculation system.

BROAD STATEMENT OF THE INVENTION

The present invention is addressed to an electrode for evaluating electrochemical potentials which has a robust structure particularly suiting it for employment within the rigorous environment of the reactor core of a nuclear power facility.

The electrode of the present invention is comprised of five major segments: a metal cap electrode, an elongated annular metal jacket, an alumina retainer (i.e. an insulator), an annular transition sleeve, and a positioning and signal transfer assembly. The metal cap electrode has a tip and annulus extending therefrom formed from sidewalls having an interior surface. The elongated annular metal jacket has an annular retainer securing mouth at one end and an outlet at its opposite end. The alumina retainer has a recessed cap securing portion nestably secured to a portion of said cap electrode interior sidewall surface, and an oppositely-disposed recessed jacket securing portion nestably secured to the interior of said annular jacket retainer securing mouth. The retainer further has an access channel penetrating therethrough from said cap to said jacket securing portion. A first insulated electrical conductor in electrical connection with the cap electrode extends through the retainer access channel and through the annular metal jacket to the jacket outlet. Finally, the positioning and signal transfer assembly is associated with the jacket outlet for providing support for said jacket and for conveying electrical signals from said conductor. An elongated annular metal transition sleeve is interposed between said jacket and said positioning and signal transfer assembly.

Advantages of the present invention include a probe structure adapted to operate under the rigorous environment of the reactor core of a nuclear power facility. Another advantage is the ceramic/metal construction of the electrode for providing a sealing architecture that has multiple seals to prevent leakage of radioactive materials to the ambient environment of the reactor. These and other advantages will be readily apparent to those skilled in the art based upon the disclosure contained herein.

BRIEF DESCRIPTION OF THE DRAWINGS

FIG. 1 is a cross-sectional elevation view of an electrode probe according to the invention;

FIG. 2 is a cross-sectional elevational view of an alternative electrode probe design according to the invention;

FIG. 3 is a cross-sectional elevational view of an alternative metal cap electrode design for use with the electrode probe of the present invention.

Figure 4:
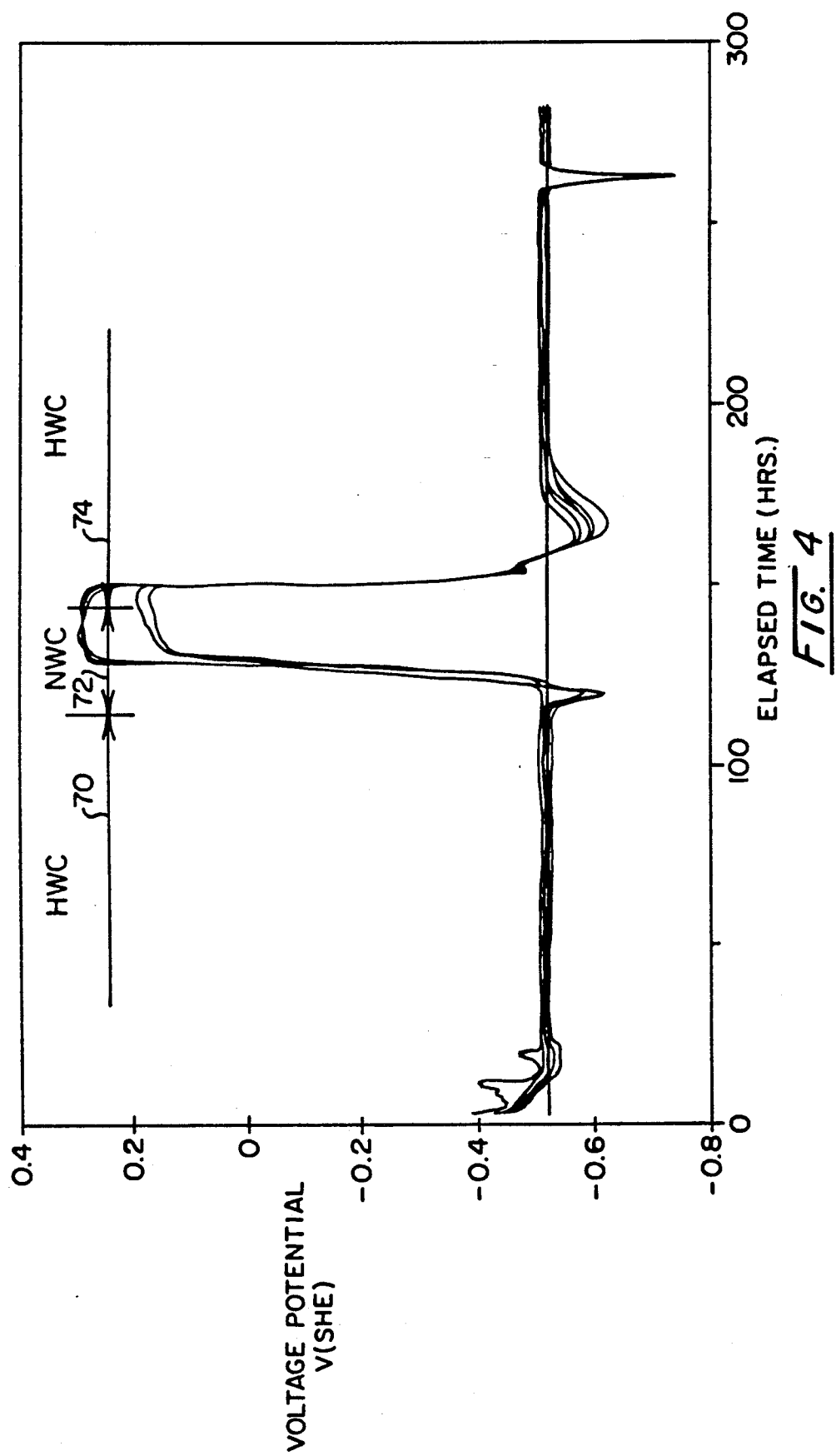
FIG. 4 is a graph showing a laboratory evaluation of five electrodes according to the invention.

The drawings will be described in detail in connection with the description that follows.

DETAILED DESCRIPTION OF THE INVENTION

While having utility in a broad variety of industrial monitoring functions, the electrode structure of the instant invention finds particular utility operating under the rigorous environment of the reactor core of a nuclear power facility. No elastomeric seals or polymeric components are present in its structure which incorporates a sealing architecture of the highest integrity. In the latter regard, a brazed and welded assembly consisting only of ceramic and metal parts forms the structure of the device. The electrode finds employment either as a standard or reference electrode, or as a sensing electrode depending upon the material used in forming the active electrode area. For a detailed discussion in connection with the above, reference is made to *Physical Chemistry*, by G. W. Castellan, Chapter 17, "Equilibria in Electrochemical Cells", pp 344–382, Addision-Wesley Publishing Co., Reading, Mass. (1964).

Referring to FIG. 1, the structure of the electrode probe of the present invention is seen to be comprised of five principal components: metal cap electrode 10; alumina retainer 12; annular metal jacket 14; annular transition sleeve 36; and positioning and signal transfer assembly 16. Electrical signals are transferred from metal cap electrode 10 through positioning and signal transfer assembly 16 to the outside via electrical conductor 18.

Referring to the various components in more detail, metal cap electrode 10 can be seen to be formed of tip portion 20 and annulus 22 that extends therefrom and which defines a cavity having interior surface 24. Materials of construction for metal cap electrode 10 will determine the function of the electrode device of the present invention. For typically-encountered boiling water reactor (BWR) applications, use of stainless steel in constructing metal cap electrode 10 enables the electrode probe to measure the ECP of stainless steel in any given environment. Metal cap electrodes fabricated from other materials could be used to form similar sensing electrodes for measurement of ECPs of different metals. The second general category for the electrode device of the present invention involves the use of platinum in fabricating metal cap electrode 10. Such an electrode device in HWC environments enables the use of the electrode device as a reference electrode (provided the hydrogen concentration is known) or it can be used to calibrate other reference electrodes (e.g. an Ag/AgCl reference electrode). Thus, it will be seen that the architecture of the electrode probe of the present invention provides design flexibility enabling it to be adapted to function both as a sensing electrode as well as a reference electrode, while retaining the same overall construction advantages.

In order to provide electrical isolation of metal cap electrode 10 from other metal components forming the electrode probe, alumina retainer 12 is used to support metal cap electrode 10. Alumina retainer 12 desirably is formed of sapphire, which is a single crystal form of alumina. Sapphire material not only provides requisite electrical insulation, but also, by virtue of its single crystal structure, is highly resistant to attack by water within which it is immersed and, importantly, it exhibits no grain boundaries. High purity alumina, ruby, or other materials, of course, can be used as those skilled in the art will appreciate. Alumina retainer 12 is seen to be formed having recessed jacket securing portion 26 and oppositely-disposed recessed cap securing portion 28. Cap securing portion 28 is nestably disposed within metal cap electrode 10 and in sealing engagement with cavity interior surface 24. Advantageously, interior surface 24 of annulus 22 is brazed to retainer cap securing portion 28, e.g. by use of silver braze. In this regard, it will be appreciated that all ceramic surfaces to be brazed are metallized, e.g. with tungsten and plated with nickel or platinum in order to ensure adequate wetting of the surfaces to be attached by the braze filler metal or alloy. In fact, use of multiple layers of metal coating, especially on interior surface 24 of recessed cap securing portion 28 of alumina retainer 12, can be practiced as is necessary, desirable, or convenient in conventional fashion. The braze seal between metal cap electrode 10 and alumina retainer 12 should provide a hermetic seal for ensuring integrity of the electrode probe structure and to ensure against leakage of radiation to the outside environment. To this end, the attachment regions of retainer 12 desirably are painted with tungsten oxide paint, fired, and then nickel or platinum plated.

Recessed jacket securing region 26 of alumina retainer 12 is nestably disposed within annular metal jacket 14. Again, surface metallization and brazing with silver braze or the like is practiced for joining attachment region 26 to jacket 14. Retainer 12 also has access channel 30 which runs its extent from cap securing portion 28 to jacket securing portion 26. Again, it will be appreciated that a hermetic seal needs to be formed. Jacket-securing portion 26, then, preferably is metallized, fired, and plated.

Annular metal jacket 14 has alumina retainer region 32 for joining with retainer jacket attachment portion 26. In the construction architecture depicted at FIG. 1, retainer 12 is formed to have land 34 against which jacket 14 rests. Retainer 12 also is formed to have land 35 against which cap 10 rests. It should be observed that the dimensional tolerances for all components to be joined is such that snug interengagement results, thus minimizing the volume to be filled by the braze metal used in joining the various components forming the electrode device of the present invention.

Jacket 14 can be formed of nickel or similar metal. Alternatively, it can be formed of a Kovar material or a similar corrosion resistant alloy for improving the matching of coefficients of thermal expansion between retainer 12 and jacket 14. Kovar materials are a group of alloys having a characteristic of expansion making it compatible with that of the alumina materials of retainer 12. One representative Kovar material comprises Fe 53.8%, Ni 29%, Co 17%, and Mn 0.2% (Hackh's Chemical Dictionary, Fourth Edition, page 374, McGraw-Hill, Inc., 1969). Heretofore, this group of alloys were employed in radio tube and thermostat construction where bonding of glass was required. Kovar alloys have been known for quite some time. Broadly, they contain from 17-18% cobalt, 28-29% nickel, with the balance being mostly iron. Their ductility and lack of embrittlement under conditions of ordinary use including heating and annealing make them useful, such as in sealing glasses, as further expounded upon by Kohn in *Electron Tubes*, pp 448 et seq. Some advantage can be achieved by the use of another material (Alloy 42) which has a similar coefficient of expansion as Kovar, but contains no added cobalt.

In the design indicated in FIG. 1, the lower end of annular metal jacket 14 is attached to annular transition sleeve 36 at juncture 38 by use of tungsten inert gas (TIG) welding techniques. Again, a hermetic seal needs to result when joining jacket 14 to sleeve 36. Annular transition sleeve 36 is seen to terminate with outlet 40 where it is attached to coaxial cable assembly 42, such as by TIG welding. Conducting wire 46 of coaxial cable assembly 42 passes through cable insulation 48 for attachment to electrical conductor 18 via welded foil 52. Foil 52 which joins electrical conductor wire 18 and conducting wire 46, provides sufficient slack to minimize manufacturing and operational stresses in the wiring which could result in loss of electrical continuity. Electrical conductor 18 is insulated from annular transition sleeve 36 and annular metal jacket 14 by ceramic insulator 54A.

The main difference between designs depicted in FIGS. 1 and 2 are the specific manufacturing arrangement of the positioning and signal transfer assembly 16 and the application of a bell shaped annular metal jacket 14. In FIG. 1, the positioning and signal transfer assembly 16 consists of conducting wire 46, cable insulation 48, coaxial cable assembly 42, and the lower portion of the annular transition sleeve 36, including outlet 40. The FIG. 2 positioning and signal transfer assembly 16 consists of the same parts defined in FIG. 1 as well as two additional parts, a seal assembly and a cable adapter. Seal assembly 68 manufactured by GE/Reuter-Stokes of Twinsburg, Ohio, consists of a ceramic to metal seal to the coaxial cable, and a ceramic insulator, and a nickel tube sealed to the ceramic insulator. The cable adapter 44 is needed to increase the effective coaxial cable outside diameter when the bell shaped annular metal jacket 14 is used with the larger outside diameter annular transition sleeve 36.

In the alternative design depicted at FIG. 2, the lower end of transition sleeve 36 is seen to terminate at outlet 40, where it is attached to the stainless steel cable adapter 44, such as by TIG welding. Cable adapter 44 is seen to terminate at outlet 50 where it is attached to coaxial cable assembly 48 and seal assembly 68 where it terminates by welding to the inside of the distal end of the nickel tube of the seal assembly. The outside of the nickel tube of the seal assembly 68 is attached to the electrical conductor wire 18 via welded foil 52. Electrical conductor wire 18 is insulated from annular transition sleeve 36 by ceramic "T" insulator 54B.

As an alternate to the designs shown in FIGS. 1 and 2, a third alternative is possible. By elimination of cable adaptor 44 in FIG. 2, but maintaining the seal assembly 68, it is possible to achieve an entire assembly without a break in the O.D. dimension similar to the O.D. dimensions in FIG. 1. In this third alternative, the "bell-shaped" annular metal jacket 14 is replaced by a constant O.D. annular metal jacket. Conductor 18 suitably can be made from nickel, Kovar, platinum, or other material which is electrically conductive. While an electrical conductor can be insulated directly, the preferred structures depicted at FIGS. 1 and 2 show annular electrical insulator 54A disposed within annular jacket 14 and annular sleeve 36. Electrical insulator 54A preferably is made from a ceramic material, such as alumina, in order to ensure electrical isolation of electrical conductor 18. While the proximal end of electrical conductor 18 is electrically connected to assembly 16, via foil 52, the distal end of electrical conductor 18 passes through the annulus formed within jacket 14 and sleeve 36, thence though access channel 30 provided in retainer 12 to cap electrode holder 10A. Conductor 18 terminates as a nail lead and is welded or brazed directly to the interior side of tip portion 20 of cap electrode 10.

The alternative cap arrangement is depicted in FIG. 3. It will be observed that tip portion 10 is formed to have elongated threaded section 56 to which electrode cap extension 58 is screwed. It will be observed that electrode cap extension 58 is formed as having tip portion 60 and annulus 62 which defines cavity 64. Interior surface 66 of annulus 62 is threaded for matching the threads of section 56. Conductor 18 then penetrates into cap electrode holder 10A for providing electrical connection thereto. Electrode cap 58 is formed from platinum or other suitable reference electrode metal and cap electrode holder 10A is formed from Kovar plated with platinum. The alternate cap arrangement can provide an advantage by way of the Kovar cap electrode holder 10A, which provides a better match of expansion coefficients with the sapphire or alumina retainer 12, than would platinum directly. The platinum electrode cap extension 58 screwed to interior surface 66 provides a sufficient surface area to obviate any holidays in the platinum plated Kovar cap electrode holder 10A.

With respect to performance specifications of the inventive electrode probe, the probe is designed to operate at temperatures ranging up to 600° F. and pressures of up to about 2,000 psi. When metal cap electrode 10 is formed of platinum for producing the reference electrode device, the novel electrode device exhibits a voltage that is within ±0.020 volts of the theoretical value for the platinum reference electrode. In use as a reference electrode platinum plated cap, the inventive electrode probe is capable of measuring ECPs to within ±0.010 volts in constant water chemistry. In attaching cap 10 manufactured of Kovar and platinum plated, it should be silver brazed to W/Ni or W/Pt coated insulator securing portion 62.

Referring to FIG. 3, five sensing electrode probes were fabricated in accordance with the precepts of the invention utilizing stainless steel for metal cap electrode 10 and these probes subjected to laboratory testing utilizing a standard $Cu/Cu_2O/ZrO_2$ reference electrode. The aqueous medium for testing was provided by an autoclave within which temperature and water chemistry were controlled. The test was carried out at a water temperature of 274° C. and in conjunction with a sequence of aqueous conditions wherein certain dissolved gases were introduced. A first such dissolved gas was hydrogen, as labeled along the elapsed time portion of the figure as represented at 70, and represents hydrogen water chemistry. Thereafter, as labeled along the elapsed time portion of the figure as represented at 72, oxygen was injected into the aqueous medium, thus subjecting the probes to normal boiling water chemistry. Finally, additional hydrogen was injected as represented at 74. As the potential of the reference electrode can be calculated, its potential under the various water conditions can be subtracted from the voltage obtained, thus enabling a measurement of the ECP of the stainless steel electrode probes. The results of the five probes evaluated are represented in FIG. 4 and can be seen to be very close in value. It will be observed that a shift in the ECP results by virtue of the water chemistry involved. It is this shift that is monitored during use of the sensing electrode probes for determining the water chemistry of the aqueous medium being tested. The expected shift in ECP can be seen by reference to FIG. 4.

Since certain changes may be made in the above-described apparatus without departing from the scope of the invention, the description and accompanying drawings shall be interpreted as illustrative and not in a limiting sense in accordance with the precepts of the invention disclosed herein.

We claim:

1. An electrode probe for employment in monitoring electrochemical potentials, comprising:
    (a) a metal cap electrode having a tip, and an annulus extending therefrom which defines a cavity having an interior surface;
    (b) an elongate annular metal jacket having an annular retainer securing mouth at one end and an outlet at its opposite end;
    (c) an alumina retainer having a recessed cap securing portion nestably disposed within said cap electrode cavity and sealingly attached thereto, and an oppositely-disposed recessed jacket securing portion nestably secured to the interior of said annular jacket retainer securing mouth, and an access channel penetrating therethrough from said cap to said jacket securing portion;
    (d) a first insulated electrical conductor in electrical connection with said cap electrode and extending through said retainer access channel and through said annular metal jacket to said jacket outlet;
    (e) a positioning and signal transfer assembly associated with said jacket outlet for providing support for said jacket and for conveying electrical signals from said conductor; and
    (f) an annular metal transition sleeve interposed between said annular metal jacket and said positioning and signal transfer assembly, said metal transition sleeve being formed of a material which is different than the material from which said annular metal jacket is formed.

2. The electrode probe of claim 2 wherein said first electrical conductor is insulated by an annular electrical insulator housed within said metal jacket.

3. The electrode probe of claim 2 wherein said annular electrical insulator is formed of alumina.

4. The electrode probe of claim 1 wherein said positioning and signal transfer assembly includes an annular stainless steel collar welded to the outlet of said annular metal transition sleeve and through which an insulated second electrical conductor passes, said second electrical conductor being electrically connected to said first electrical conductor.

5. The electrode probe of claim 1 wherein said first electrical conductor is attached to said positioning and signal transfer assembly with metal foil.

6. The electrode probe of claim 1 wherein said metal transition sleeve is formed of stainless steel.

7. The electrode probe of claim 1 wherein said first electrical conductor is a wire formed of a material selected from the group consisting of platinum, nickel, and an alloy comprising by weight from about 17–18% cobalt, 28–29% nickel, and the balance mostly iron.

8. The electrode probe of claim 1 wherein said metal cap electrode is formed of a material selected from the group consisting of stainless steel and platinum.

9. The electrode probe of claim 1 wherein said alumina retainer is formed from single crystal sapphire.

10. The electrode probe of claim 1 wherein said metal cap electrode tip has a threaded extension and said electrode probe further comprises a metal cap electrode extension having a tip portion and an interiorly threaded annulus extending therefrom, said metal cap electrode threaded extension and said metal cap electrode extension threaded annulus being threadingly interengaged.

11. An electrode probe for employment in monitoring electrochemical potential, comprising:
    (a) a cylindrical metal cap electrode having a tip, and an annulus extending therefrom which defines a cavity having an interior surface;
    (b) a cylindrical elongate annular metal jacket having an annular retainer securing mouth at one end and an outlet at its opposite end;
    (c) a cylindrically-shaped alumina retainer having a cap securing portion nestablty disposed within said cap electrode cavity and sealingly attached thereto, and an oppositely-disposed recessed jacket securing portion nestably secured to the interior of said annular jacket retainer securing mouth, and an access channel penetrating therethrough from said cap to said jacket securing portion;
    (d) an annular ceramic electrical insulating cylinder housed within said jacket;
    (e) a first electrical conductor in electrical connection with said cap electrode and extending through said retainer access channel and through said annular metal jacket to said jacket outlet;
    (f) a stainless steel annular transition sleeve welded to the outlet of said annular jacket, said transition sleeve having an outlet; and
    (g) a positioning and signal transfer assembly associated with transition sleeve outlet for providing support for said jacket and for conveying electrical signals from said first conductor.

12. The electrode probe of claim 11 wherein said alumina retainer is formed of a single crystal sapphire.

13. The electrode probe of claim 12 wherein said first conductor comprises a wire which is formed of a material selected from the group consisting of platinum, nickel, and an alloy comprising by weight from about 17–18% cobalt, 28–29% nickel, and the balance mostly iron.

14. The electrode probe of claim 13 wherein said metal cap electrode is formed from a material selected from the group consisting of stainless steel and platinum.

15. The electrode probe of claim 14 wherein said assembly includes a metal collar welded to the outlet of said annular jacket.

16. The electrode probe of claim 13 wherein the surfaces of the alumina retainer to be joined to the cap electrode and to the annular metal jacket are metallized.

17. The electrode probe of claim 11 wherein said first conductor comprises a wire which is electrically joined to the signal transfer assembly by welded interposed metal strips in the annular ceramic cylinder between said first conductor and said signal transfer assembly.

18. The electrode probe of claim 11, wherein said metal cap electrode tip has a threaded extension and said electrode probe further comprises a metal cap electrode extension having a tip portion and an interiorly threaded annulus extending therefrom, said metal cap electrode threaded extension and said metal cap electrode extension threaded annulus being threadingly interengaged.

* * * * *